United States Patent
Miao et al.

(10) Patent No.: US 11,621,059 B2
(45) Date of Patent: Apr. 4, 2023

(54) METHOD FOR ON-LINE PREDICTION OF CONJUNCT POLYMER CONCENTRATION IN A HYDROCARBON CONVERSION PROCESS

(71) Applicant: CHEVRON U.S.A. INC., San Ramon, CA (US)

(72) Inventors: Toni Zhang Miao, Orinda, CA (US); Huping Luo, Moraga, CA (US); Hye-Kyung Cho Timken, Albany, CA (US); Eddy Lee, Hercules, CA (US); Bong-Kyu Chang, Novato, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 82 days.

(21) Appl. No.: 17/325,310

(22) Filed: May 20, 2021

(65) Prior Publication Data

US 2022/0036976 A1 Feb. 3, 2022

Related U.S. Application Data (60) Provisional application No. 63/059,248, filed on Jul. 31, 2020.

(51) Int. Cl.
| | |
|---|---|
| *G16C 20/70* | (2019.01) |
| *G16C 10/00* | (2019.01) |
| *G16C 20/30* | (2019.01) |
| *C07C 2/76* | (2006.01) |
| *G01N 21/3577* | (2014.01) |
| *G01N 33/28* | (2006.01) |
| *C07C 2/66* | (2006.01) |
| *C07C 2/64* | (2006.01) |
| *G01N 21/35* | (2014.01) |

(Continued)

(52) U.S. Cl.
CPC ............... *G16C 20/70* (2019.02); *C07C 2/64* (2013.01); *C07C 2/66* (2013.01); *C07C 2/76* (2013.01); *G01N 21/3577* (2013.01); *G01N 33/28* (2013.01); *G16C 10/00* (2019.02); *G16C 20/30* (2019.02); *B01J 2219/00047* (2013.01); *C07C 2/68* (2013.01); *C07C 2/70* (2013.01); *G01N 2021/3595* (2013.01)

(58) Field of Classification Search
CPC ........ G01C 20/70; G01C 10/00; G01C 20/30; C07C 2/64; C07C 2/66; C07C 2/76; C07C 2/68; C07C 2/70; G01N 33/28; G01N 2021/3595; G01N 2021/8411; G01N 21/552; G01N 2201/129; B01J 2219/00047
See application file for complete search history.

(56) References Cited

U.S. PATENT DOCUMENTS 5,681,749 A * 10/1997 Ramamoorthy ... G01N 21/3577
436/171
9,290,702 B2 3/2016 Lacheen
(Continued)

FOREIGN PATENT DOCUMENTS

EP 1040336 B1 5/2007

OTHER PUBLICATIONS

PCT International Search Report, International Appl. No. PCT/IB2021/054355, dated Jul. 26, 2021.

*Primary Examiner* — Ali Z Fadhel (57) ABSTRACT

A method is provided for predicting conjunct polymer concentration in spent ionic liquid during a continuous hydrocarbon conversion process.

11 Claims, 8 Drawing Sheets

(51) Int. Cl.
*C07C 2/68* (2006.01)
*C07C 2/70* (2006.01)

(56) References Cited

U.S. PATENT DOCUMENTS

| | | |
|---|---|---|
| 10,094,778 B1* | 10/2018 | Luo .................... G01N 21/3577 |
| 10,113,963 B1 | 10/2018 | Luo et al. |
| 10,352,770 B2* | 7/2019 | Morales Rodriguez ..................... G01N 21/85 |
| 2012/0296145 A1* | 11/2012 | Lacheen .............. B01J 31/0284 436/98 |
| 2015/0276645 A1* | 10/2015 | Buchbinder ......... B01J 31/0277 205/775 |
| 2015/0276692 A1* | 10/2015 | Olson ..................... B01J 19/18 436/37 |
| 2015/0316519 A1* | 11/2015 | Martins .................. G01N 31/22 436/101 |
| 2018/0180555 A1* | 6/2018 | Zhang .................... G01N 21/79 |
| 2018/0188159 A1* | 7/2018 | Liu ...................... B01J 31/0279 |

* cited by examiner

METHOD FOR ON-LINE PREDICTION OF CONJUNCT POLYMER CONCENTRATION IN A HYDROCARBON CONVERSION PROCESS

FIELD

This disclosure relates generally to methods for analyzing spent ionic liquids in integrated, catalytic hydrocarbon conversion systems such as continuous alkylation systems.

BACKGROUND

Acidic ionic liquid may be used as a catalyst in various hydrocarbon conversion reactions, such as for the alkylation of isobutane with olefins, olefin oligomerization, paraffin disproportionation, paraffin isomerization and aromatic alkylation. A byproduct of these reactions is the accumulation, over time, of conjunct polymer in the liquid catalyst. As would be appreciated, conjunct polymer is typically highly olefinic, conjugated, highly cyclic hydrocarbons that form as a byproduct of various hydrocarbon conversion processes, including but not limited to alkylation, oligomerization, isomerization, and disproportionation.

Due to the olefinic and di-olefinic functionality of conjunct polymer, it has a strong affinity for the acidic ionic liquid catalyst. This results in the catalyst losing acidity as the amount of conjunct polymer in ionic liquid catalyst increases. If acidity of the ionic liquid catalyst is reduced, the effectiveness of the catalyst in the reaction zone will be reduced as well.

Used (or spent) ionic liquid catalyst containing some conjunct polymer is typically recycled back into the reaction zone and a slip stream is typically diverted to a regeneration zone, in order to maintain a constant level of catalyst activity.

The ionic liquid catalyst can be regenerated by several processes. However, it still must be determined if the ionic liquid catalyst should be regenerated, or if the ionic liquid catalyst can be recycled back to the reaction zone.

This disclosure features methods for determining in real-time or near real-time analyte properties such as conjunct polymer concentrations in spent ionic liquid using an infrared spectrometer that is integrated in-line with hydrocarbon conversion systems and coupled to an electronic controller that analyzes information measured by the spectrometer. Infrared spectra of the solutions can be monitored continuously, and chemometric models are used to accurately characterize quantitative chemical and/or physical properties of the analytes simultaneously in solution. Spectra can be obtained in-line from flowing solutions so that measurements are performed with little or no disruption to hydrocarbon conversion processes. Further, the chemometric models can extract quantitative analyte information in real time or near-real time, permitting rapid feedback and control over process-related parameters and operations.

SUMMARY

In one aspect, there is provided a method for predicting a concentration of conjunct polymer in a spent ionic liquid of unknown conjunct polymer concentration during a continuous hydrocarbon conversion process, the method comprising: (a) separating an effluent from a reaction zone into a light fraction and a heavy fraction, the heavy fraction comprising spent ionic liquid of unknown conjunct polymer concentration; (b) acquiring an infrared spectrum for each of a plurality of samples of the spent ionic liquid using an in-line infrared spectrometer configured with a measurement cell to allow the spent ionic liquid to flow therethrough; (c) separately determining a concentration of conjunct polymer in the spent ionic liquid by acquiring an infrared spectrum for each of a plurality of samples using an off-line infrared spectrometer; (d) analyzing the infrared spectra acquired in (b) and (c) using a multivariate chemometric technique to provide a training data set; (e) generating a predictive model for conjunct polymer concentration based on the training data set; (f) applying the predictive model to the infrared spectra acquired in (b); and thereafter (g) quantitatively predicting the conjunct polymer concentration in the spent ionic liquid during the continuous hydrocarbon conversion process.

DETAILED DESCRIPTION

Definitions

"Ionic liquid" refers to salts (i.e., compositions comprising cations and anions) that are liquid at a temperature of at or below about 150° C. (e.g., at or below about 120° C., 100° C., 80° C., 60° C., 40° C., or 25° C.). An ionic liquid is not considered a mere solution containing ions as solutes dissolved therein.

"Fresh ionic liquid" refers to an active ionic liquid catalyst that has not been used for any application, such as new catalyst received from a vendor.

"Spent ionic liquid" refers to ionic liquid catalyst removed from a reaction zone that includes conjunct polymer and which has not been passed to a regeneration zone and which may include regenerated ionic liquid catalyst that has been reused in the reaction process as a catalyst.

"Regenerated ionic liquid" denotes an ionic liquid catalyst that had become spent and was then subjected to a process that increased its activity to a level greater than it had as a spent catalyst. The regenerated ionic liquid typically has an activity that is equal or less than the fresh ionic liquid catalyst activity.

"Conjunct polymer" refers to materials containing olefinic, conjugated and cyclic hydrocarbons that form as a byproduct of various hydrocarbon conversion processes, including but not limited to alkylation, oligomerization, isomerization, and disproportionation.

"In-line" refers to a device (e.g., an infrared spectrometer) placed at a regular fluid flow line.

"Off-line" refers to a device (e.g., an infrared spectrometer) placed at a stream of batch fluid that has been extracted from a regular fluid flow line, a bypass stream, or a pit (e.g., the batch fluid is circulated in a loop).

"Continuous" means a system that operates without interruption or cessation. For example, a continuous process to produce a alkylate would be one where the reactants are continually introduced into one or more reactors and alkylate product is continually withdrawn until the alkylation is stopped.

"Real-time" refers to measurements or processes that occur with a relatively small delay or recurrence period. For example, "real-time" measurements are measurements for which a total elapsed time interval between the beginning of the measurement of spectroscopic information and the time at which a parameter value or other quantity is calculated from the information is 1 minute or less. Periodic real-time measurements are recurring/periodic measurements with a time interval of 1 minute or less between successive measurements.

"Near real-time" measurements are measurements for which a total elapsed time interval between the beginning of the measurement of spectroscopic information and the time at which a parameter value or other quantity is calculated from the information is between 1 minute and 5 minutes. Periodic near real-time measurements are recurring/periodic measurements with a time interval of between 1 minute and 5 minutes between successive measurements.

"Attenuated total reflection" (ATR) is a sampling technique used in conjunction with infrared spectroscopy which enables samples to be examined directly in the solid or liquid state without further preparation.

A "distributed control system" (DCS) is a computerized control system for a process or plant, in which autonomous controllers are distributed throughout the system, but there is central operator supervisory control.

A "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

Introduction

According to the present disclosure, one or more of the following parameters can be controlled based upon a predicted conjunct polymer concentration in the spent ionic liquid determined during a continuous hydrocarbon conversion process: an amount of spent ionic liquid passed back to a reaction zone; an amount of spent ionic liquid passed to a regeneration zone; an amount of fresh ionic liquid passed to the reaction zone; and an amount of spent ionic liquid removed from the continuous hydrocarbon conversion process.

Prediction of conjunct polymer concentration in the spent ionic liquid according to the present disclosure may be repeated and it may be repeated as long as the hydrocarbon conversion process is maintained.

It is contemplated that a desired conjunct polymer concentration range of the spent ionic liquid is maintained.

It is contemplated that a portion of the spent ionic liquid is passed to a regeneration zone to provide a regenerated ionic liquid.

It is contemplated that the portion of the spent ionic liquid returned to a reaction zone is lowered if the concentration of conjunct polymer in the spent ionic liquid is above a desired concentration range. A fresh ionic liquid, a regenerated ionic liquid, or both may be also passed to the reaction zone if the concentration of conjunct polymer in the spent ionic liquid is above the desired concentration range.

Hydrocarbon Conversion

The hydrocarbon conversion process involves contacting a hydrocarbon feed with an ionic liquid catalyst in a reaction zone under hydrocarbon conversion conditions. The effluent from the reaction zone is then separated into a heavy portion containing spent ionic liquid catalyst and a light portion containing the reaction products. The separation may occur by gravity, by coalescing, by both, or by otherwise recovering the droplets of spent ionic liquid catalyst.

Typical hydrocarbon conversion processes include alkylation, oligomerization, isomerization, and disproportionation.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.).

Processes for the oligomerization of light olefins (e.g., ethylene, propylene, and butylene) to produce higher carbon number olefin products (e.g. C6+ olefins) are well known. Oligomerization processes have been employed to produce high quality motor fuel components as well as petrochemicals from ethylene, propylene, and butylene. Suitable hydrocarbon feed for isomerization reactions includes C2 to C23 olefins.

Isomerization of linear paraffins to their branched isomers increases their octane number and thus their value to a refiner. Isomerization processes involve reacting one mole of a hydrocarbon (e.g., normal pentane) to form one mole of an isomer of that specific hydrocarbon (e.g., isopentane). The total number of moles remains the same throughout this process, and the product has the same number of carbons as the reactant. Suitable hydrocarbon feed for isomerization reactions includes C3 to C23 paraffins.

The disproportionation of paraffins (e.g., isopentane) involves reacting two moles of hydrocarbon to form one mole each of two different products, one having a carbon count greater than the starting material and the other having a carbon count less than the starting material. The total number of moles in the system remains the same throughout the process, but the products have different carbon counts from the reactants. Suitable hydrocarbon feeds for disproportionation reactions include C2 to C23 paraffins. Feeds comprising two or more paraffins are also acceptable.

The hydrocarbon conversion conditions depend on the particular hydrocarbon conversion process. The reaction temperature is typically in a range of from −20° C. to 250° C. The pressure is typically in a range of from 0 MPa (g) to 13.8 MPa (g)

Figure 1:
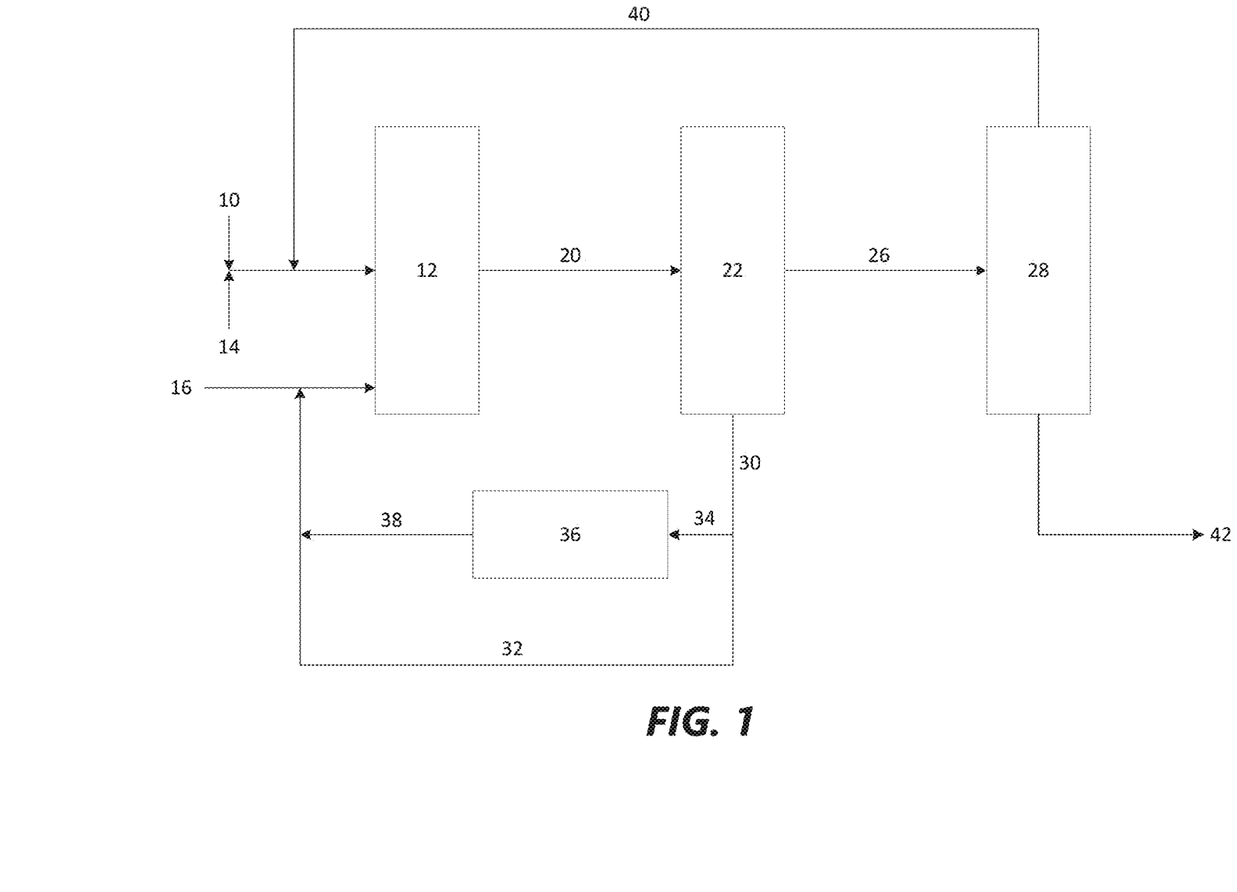
FIG. 1 illustrates a hydrocarbon conversion process, according to some aspects of the disclosure herein.

FIG. 1 illustrates one aspect of a hydrocarbon conversion process of the present disclosure showing an example of an ionic liquid catalyzed alkylation zone for the manufacture of alkylate gasoline blending components. With reference to FIG. 1, a hydrocarbon feed 10 is passed into a reaction zone 12. The hydrocarbon feed 10 typically includes a mixture of olefins, paraffins, and isoparaffins, and they may be separately added to the reaction zone 12 in one or more locations. Thus, the hydrocarbon feed 10 comprises an olefin stream of olefins. Additionally, an isoparaffin stream of isoparaffins 14 is also passed to the reaction zone 12. An ionic liquid stream 16 is also passed to the reaction zone 12. The reaction zone 12 includes at least one reactor for an alkylation reaction.

In general, an alkylation process includes passing an isoparaffin and an olefin to an alkylation reactor, where the alkylation zone 12 includes an ionic liquid catalyst to react the olefin with the isoparaffin to generate an alkylate. The paraffin used in the alkylation process preferably comprises an isoparaffin having from 4 to 10 carbon atoms (e.g., 4 to 8 carbon atoms, or 4 to 5 carbon atoms). The olefin used in the alkylation process preferably has from 2 to 10 carbon atoms (e.g., 3 to 8 carbon atoms, or 3 to 5 carbon atoms). The isoparaffin has from 4 to 10 carbon atoms, and the olefin has from 2 to 10 carbon atoms. According to one or more aspects of the present disclosure, the alkylation process upgrades relatively low value C4 hydrocarbons to higher value alkylates. To that extent, one specific aspect is the alkylation of butanes with butylenes to generate C8 compounds. Preferred products include trimethylpentane (TMP), and while other C8 isomers are produced, one competing isomer is dimethylhexane (DMH). The quality of the product stream can be measured in the ratio of TMP to DMH, with a high ratio desired.

Typical alkylation reaction conditions include a temperature in the range of from −20° C. to the decomposition temperature of the ionic liquid, or from −20° C. to 100° C. (e.g., from −20° C. to 80° C., or from 0° C. to 80° C., or from 20° C. to 80° C., or from 20° C. to 70° C., or from 20° C. to 50° C.). Ionic liquids can also solidify at moderately low temperatures, and therefore it is preferred to have an ionic liquid that maintains its liquid state through a reasonable temperature span. In some aspects, cooling may be needed. If cooling is needed, it can be provided using any known methods. The pressure is typically in a range of from 0.1 to 8.0 MPa(g), or from 0.3 to 2.5 MPa(g). The pressure is preferably sufficient to keep the reactants in the liquid phase. The residence time of the reactants in the reaction zone 12 is in a range of a few seconds to hours (e.g., 0.5 min to 60 min, or 1 min to 60 min, or 3 min to 60 min).

Due to the low solubility of hydrocarbons in ionic liquids, olefins-isoparaffins alkylation, like most reactions in ionic liquids is generally biphasic and takes place at the interface in the liquid state. The catalytic alkylation reaction is generally carried out in a liquid hydrocarbon phase, in a batch system, a semi-batch system or a continuous system using one reaction stage as is usual for aliphatic alkylation. The isoparaffin and olefin can be introduced separately or as a mixture. The molar ratio between the isoparaffin and the olefin is in a range of from 1:1 to 100:1 (e.g., from 2:1 to 50:1, or from 2:1 to 20:1).

The ionic liquid comprises an organic cation and an anion. Suitable organic cations include nitrogen-containing cations and phosphorus-containing cations. Suitable organic cations include ammonium cations, pyridinium cations, imidazolium cations, and phosphonium cations.

Suitable anions include metal halide anions, non-metal halide anions, and combinations thereof. The metal halide anion and/or non-metal halide can include at least one halide selected from F, Cl, Br, and I. In some aspects, the metal halide anion comprises a metal chloride. In some aspects, the non-metal halide anion comprises a non-metal fluoride. Exemplary non-metal halide anions include tetrafluoroborate, hexafluorophosphate, and bis(trifluoromethanesulfonyl)imide.

The metal in the metal halide anion can include a metal selected from a Group 13 metal, a transition metal, or a combination thereof. In some aspects, the metal can be selected from aluminum, gallium, indium, titanium, zirconium, chromium, iron, copper, zinc, tin, and combinations thereof. In some aspects, the metal halide anion comprises an aluminum halide.

In some aspects, the metal halide anion can be selected from chloroaluminate, chlorogallate, chloroindate, chlorotitanate, chlorozirconate, chlorochromate, chloroferrate, chlorocuprate, chlorozincate, chlorostannate, and combinations thereof. In some aspects, the metal halide anion can comprise chloroaluminate. In some aspects, the metal halide anion can comprise $[Al_2Cl_7]^-$, $[AlCl_4]^-$ or $[Ga_2Cl_7]^-$.

In some aspects, the ionic liquid is selected from the group consisting of a tetraalkylammonium chloroaluminate, a 1-alkylpyridinium chloroaluminate, a 1,3-dialkylimidazolium chloroaluminate, a tetraalkylphosphonium chloroaluminate, and combinations thereof. Exemplary ionic liquids include 1-butylpyridinium chloroaluminate, 1-butyl-3-methylimidazolium chloroaluminate, and combinations thereof.

Returning to FIG. 1, an effluent 20, including hydrocarbon conversion products, the ionic liquid catalyst, and unconverted reactants, any catalyst promoter such as hydrogen chloride, organic chlorides, or other compounds, is passed from reactor 12 to a separation zone 22 having one or more separation vessels. In the separation zone 22, the effluent 20 separates into a hydrocarbon phase and an ionic liquid phase. This separation may be a phase separation as a result of the difference in the density of the hydrocarbon phase and the ionic liquid phase, although other methods could also be used, including for example, a coalescer material. Accordingly, an alkylate effluent stream 26 is sent to product recovery section 28. A spent ionic liquid catalyst stream 30 which typically includes some amount of conjunct polymer is also recovered from the separation zone 22. A first portion 32 of the spent ionic liquid catalyst stream 30 may be recycled directly to the reaction zone 12, while a second portion 34 of the spent ionic liquid catalyst stream 30 is passed to a regeneration zone 36 to remove at least some of the conjunct polymer from the ionic liquid catalyst. Regenerated ionic liquid 38 may be passed back to the reaction zone 12.

In the product recovery zone 28, the alkylate effluent stream 26 is separated into an alkylate product 42 and a recycle hydrocarbon 40 comprising unreacted hydrocarbons including iC4 and some lighter compounds, including HCl, which is then returned to the reaction zone 12 as a recycle stream.

Conjunct polymer is bound with the spent ionic liquid catalyst as an integrated compound. The conjunct polymer does not wash off from the spent ionic liquid catalyst via simple hydrocarbon solvent extraction. It is believed that the most efficient and effective process to reduce the conjunct polymer content in the spent ionic liquid catalyst is to convert the conjunct polymer species into extractable forms of hydrocarbons (i.e., light hydrocarbon gas or saturated hydrocarbon that is not very soluble in ionic liquid) and then separate or extract the hydrocarbons from the regenerated ionic liquid catalyst. During the regeneration process, a portion of the conjunct polymer may be hydrocracked to a light material (C1-C4 hydrocarbons) which may be incorporated into the offgas, a portion may be hydrocracked to a liquid hydrocarbon stream which may be incorporated into the alkylate gasoline product, and/or a portion may be hydrocracked to HCl gas.

As long as the level of conjunct polymer in the spent ionic liquid is low enough that the effectiveness of the ionic liquid is not greatly negatively impacted, the spent ionic liquid may be returned back to the reaction zone 12 and reused as ionic liquid catalyst in the reaction zone 12. The present disclosure is directed to monitoring the amount of conjunct polymer in the spent ionic liquid in real-time or near real-time using in-line infrared spectroscopy.

The infrared spectrometer is disposed in-line, meaning that the spectrometer is either disposed (i.e., located) within a line through which the spent ionic liquid passes or is in a position to directly measure spectroscopic information in separation zone 22 in which the spent ionic liquid is a separate phase. Accordingly, the spectrometer may be disposed within any of lines 30, 32, 34 used to pass spent ionic liquid back to the reaction zone 12. It is contemplated that more than one infrared spectrometer is used and that spectrometers are located in different places throughout the process.

For example, when the present method indicates a high concentration of conjunct polymer, a first portion of the spent ionic liquid may be returned back to the reaction zone 12, while at the same time a second portion of the spent ionic liquid catalyst is passed to the regeneration zone 36. Once the concentration of conjunct polymer returns to a desired level, the flow of the spent ionic liquid catalyst can be adjusted accordingly so that more of the spent ionic liquid catalyst is recycled back to the reaction zone 12 and less is passed to the regeneration zone 36, or, all of the spent ionic liquid catalyst is returned back to the reaction zone 12.

Figure 2:
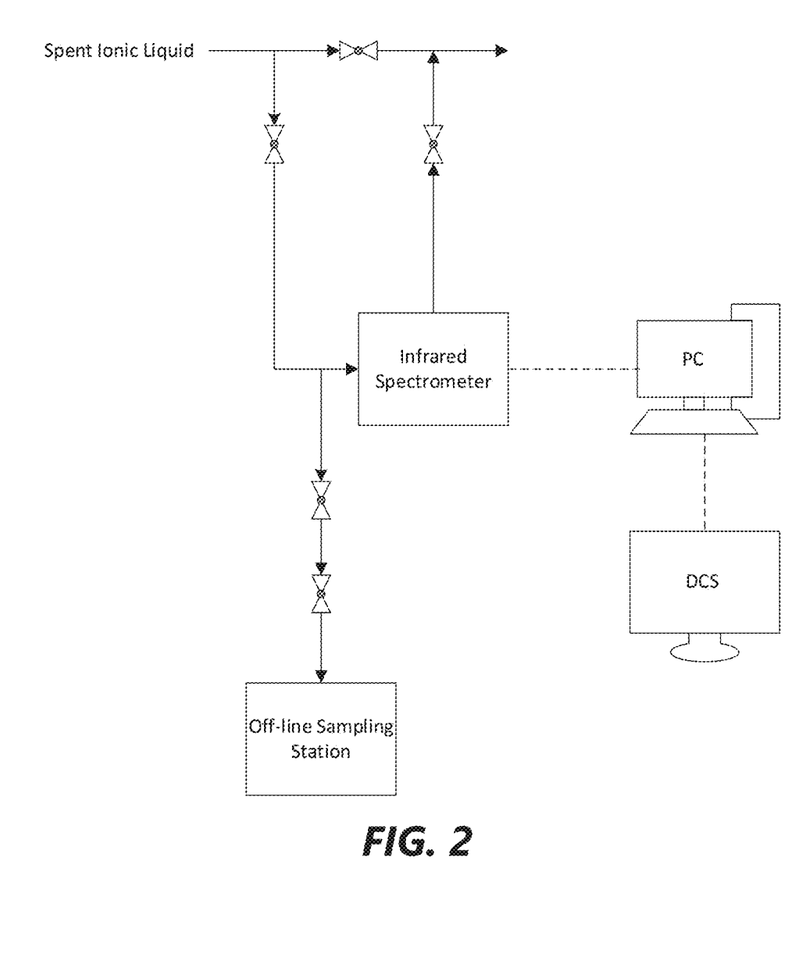
FIG. 2 is a simplified schematic drawing of an exemplary configuration of a conjunct polymer (CP) monitoring system, according to some aspects of the disclosure herein.

FIG. 2 is a simplified schematic drawing of a configuration of a system for monitoring conjunct polymer, according to some aspects of the disclosure herein. Spent ionic liquid can be directed to an off-line sampling station and/or an in-line infrared spectrometer. The spectrometer can be a FTIR spectrometer that receives reflected radiation and generates spectral information for the reflected radiation. One suitable FTIR spectrometer for use as the detector is a Bruker ALPHA II FTIR (available from Bruker Optics, Billerica, Mass.), with a deuterated triglycine sulfate (DTGS) infrared sensor, although many other FTIR spectrometers can also be used. The spectrometer is connected to a personal computer (PC) via a data link, such as an ethernet cable or Wi-Fi network. The PC may be in a separate analyzer building from a location of the spectrometer. The PC may be connected via a data link to a distributed control system (DCS).

Infrared Spectroscopic Measurements and Measurement Systems

As mentioned above, in-line infrared spectroscopy may be used to quantitatively measure conjunct polymer in spent ionic liquids. Preferably, an internal reflectance FTIR method is used for "in-situ" measurement of the infrared spectrum absorbed by the spent ionic liquid in or exiting one or more of the processing zones or vessels. The internal reflectance FTIR method allows for the infrared spectrum absorbed by the reaction solution to be measured in place by locating a sensor probe in, on or in proximity to a process line or process vessel so that it is immersed in the spent ionic liquid or positioned on a direct or reflected line of sight to the spent ionic liquid thus allowing the spent ionic liquid to be directly scanned in substantially real time without removing a sample of the solution from the vessel or process line in which it is contained. Advantageously in-situ measurements provide real-time or near real-time measurements of the spent ionic liquid.

In general, internal reflectance relates to a process wherein an infrared light beam is modulated using an interferometer, and the modulated beam is reflected off a sample and returned to a detector wherein the spectral regions absorbed as well as the intensity of the absorbance within those regions is determined. One technique for practicing the internal reflectance method is attenuated total reflectance (ATR) spectrometry which measures the absorbance in a thin layer of the sample in contact with the sampling surface of a sensor device. That is, a sensor probe is placed in direct contact with the sample. A modulated infrared beam is transmitted from the FTIR spectrometer to the sensor probe wherein the beam is transmitted through a sampling surface on the probe such that the beam penetrates into a thin layer of the sample in contact with the sampling surface of the probe and is reflected back into the sensor probe. Significantly, the beam is modified by the sample due to the absorbance characteristics of the sample. The modified beam is then optically transmitted to the FTIR spectrometer's detector. Depending on the ATR probe selected (i.e., the optical characteristics and geometry of the sampling surface), the modulated infrared beam may reflect off of both the sample layer and the sampling surface a number of times before finally returning back into the sensor probe, providing additional data to the detector. Thus, ATR probes are typically described by the number of reflections that occur through the sample layer. Preferably, the ATR probe utilizes at least about 3, more preferably at least about 6 and still more preferably at least about 9 reflections or greater.

Preferably, the sampling surface of the ATR probe is comprised of diamond. ATR probes comprising a diamond sampling surface may further comprise an additional optical element which acts both as a support for the diamond, and for transmitting and focusing the modulated infrared beam to and from the diamond sampling surface. Since the second optical element is not in contact with the reaction solution, it is less important that the second optical element have the corrosion and abrasion resistance as the sampling surface. Zinc selenide crystals have similar optical qualities as diamond at a substantially reduced cost. Accordingly, zinc selenide may be used as an additional optical element.

The sampling surface of the ATR probes may be concave, convex or have a relatively flat surface curvature. Preferably, the sampling surface of the ATR probe is relatively flat. Without being held to a particular theory, it is believed that sampling surfaces having a significant degree of curvature tend to promote the adherence of particulates to the sampling surface thereby interfering with the sensor.

The FTIR spectrometer detects the intensity or amplitude of the modified beam across the infrared region and transforms the data into an absorbance spectrum, i.e., absorbance vs. wavenumber. FTIR spectrometers typically use two types of detectors, a mercury cadmium telluride (MCT) detector or a deuterated triglycine sulfate (DTGS) detector. Although MCT detectors tend to be faster than DTGS detectors and have a high sensitivity, MCT detectors typically require a liquid nitrogen or thermoelectric cooling system, which make them inconvenient to use and economically undesired.

Spent ionic liquid is typically sampled over a spectral range of wavelengths from 2 to 50 microns (i.e., wavenumbers ranging from 200 cm$^{-1}$ to 5000 cm$^{-1}$, or from 650 cm$^{-1}$ to 4000 cm$^{-1}$, with wavenumber being the reciprocal of wavelength and proportional to frequency). The infrared spectrum is a continuous spectrum, however for analytical reasons, discrete wavenumbers or groups of wavenumbers are typically measured. The wavenumber resolution (i.e., the range of wavenumbers that are grouped together for each discrete measurement) may be increased or decreased to affect the signal to noise ratio of the FTIR spectrometer. That is, as the numerical value of the wavenumber resolution is decreased, more measurements are taken across the spectrum and the resolution of the spectrum increases. However, increases in the wavenumber resolution also typically results in a corresponding increase in the level of "noise". Generally, FTIR spectroscopy methods use wavenumber resolutions having a numerical value of 2, 4, 8 or 16 (i.e., sample data are collected over discrete ranges of 2, 4, 8 or 16 wavenumbers with the resolution being inversely proportional to the numerical value of the wavenumber resolution). Typically, a wavenumber resolution of 4 appears to provide a spectrum with a fairly good resolution while minimizing the amount of "noise." Changes in the wavenumber resolution may be made, however, without departing from the scope of the present disclosure.

Additionally, FTIR spectroscopy generally utilizes a number of scans providing additional interferometric data, i.e., intensity vs. wavenumber data used in the Fourier transform to produce the spectral data, i.e., absorbance vs. wavenumber. If the number of scans is set at 32, for example, the spectrometer will scan the entire wavelength range specified 32 times and produce 32 interferograms, or 32 intensity measurements per wavenumber, or more precisely, per wavenumber grouping as determined by the wavenumber resolution. Fourier transforms then combine the intensity data and convert the 32 interferograms into a single absorbance spectrum. The number of spectra, i.e., scans can also affect the signal to noise ratio. Generally, about 32 scans may be sampled with a new spectrum measurement being generated about every 25 seconds.

Chemometrics-Based Analysis of Infrared Spectroscopic Information

A single analyte will produce a spectrum having an absorbance profile characteristic of that analyte. That is, the spectrum contains absorbance features that may be associated with the analyte. Accordingly, the concentration of the analyte may be determined using a mathematical model representing the relationship between the concentration of the analyte and the absorbance profile. The mathematical model may be developed by measuring the spectrum for a number of standard samples having known concentrations and mathematically correlating the concentration as a function of the absorbance profile using a number of correlation methods. Unfortunately, the characteristic spectrum for a mixture of analytes such as spent ionic liquid containing conjunct polymer is more complex in that the characteristic absorbance spectrum for the various analytes are broad and overlap significantly. This overlap precludes the use of simple univariate correlation methods for quantitation of the analytes in a reaction mixture. This problem may be overcome by applying more powerful multivariate mathematical correlation techniques to the analysis of the spectral data. These multivariate mathematical techniques when applied to process chemical analysis are collectively referred to as chemometrics. This technique uses complex mathematics such as matrix vector algebra and statistics to extract quantitative information (e.g., concentrations) from highly convoluted or statistically confounded data such as the spectrum obtained from a mixture of analytes to develop a mathematical model, also called a chemometric model representing the quantitative information as a function of the spectrum. A number of multivariate mathematical techniques have been developed such as K-Nearest Neighbors analysis (KNN), Hierarchical Cluster Analysis (HCA), Principal Component Analysis (PCA), Partial Least Squares (PLS) analysis, and Principal Component Regression (PCR) analysis. Commercially available software packages are capable of performing many of the multivariate mathematical correlation techniques listed above.

Commercially available FTIR spectrometers often include chemometric analysis software. In particular, PLS and PCR are typically used for determining a chemometric model and applying it to a FTIR spectral measurement to calculate a property of the sample measured. Of these two, PLS is most commonly applied to FTIR spectral data because it generally provides the most accurate chemometric models. PLS allows each analyte to be modeled separately, and only requires knowledge of the particular analyte being modeled. That is, it does not require that the concentration of each absorbing analyte be known as long as each absorbing analyte is represented in the standards used for developing the chemometric model. Advantageously, the standards can be taken directly from the process and need not be separately prepared, thus allowing consideration of the impurity profile of the spent ionic liquid when determining the chemometric model for each analyte to be measured. However, it should be noted that the absorbance of the spectral regions is generally non-linear with respect to concentrations. Thus, the chemometric models correlating the concentration and the absorbance spectrum should be developed over particular ranges of concentration for the individual analytes of the reaction solution. That is, the standards used in the chemometric analysis should be representative of the matrix of concentrations for each analyte in the reaction solution.

In general, therefore, a number of standards are analyzed using the infrared spectrometer to measure the spectrum for each standard. The concentration of a particular analyte can then be mathematically modeled as a function of the spectra obtained i.e., an algorithm is developed that correlates the concentration and the spectrum. Although any of the multivariate mathematical calibration techniques may be used, a preferred embodiment uses the PLS method to model the spectra as a function of concentration. The number of standards used is preferably at least about 10 and more preferably at least about 20. In general, the accuracy of the model increases with increases in the number of standards used to generate the model. Therefore, the number of standards used to generate the model may be as high as 50 or greater. Such standards may be prepared mixtures, or alternatively, may be samples of the particular process mixture to be analyzed. However, as stated earlier, it is preferred that the process mixture is used such that the impurity profile is considered in the PLS analysis when generating the chemometric model. The concentration of the analyte being modeled in each standard may be measured off-line using standard analytical techniques such as high-performance liquid chromatography (HPLC). Accordingly, chemometric models may be generated using a partial least squares regression analysis for spectra obtained from reaction mixtures from either a batch or a continuous alkylation process based on-line spectral measurements and off-line HPLC concentration measurements.

As stated earlier, the FTIR scans the spent ionic liquid over a spectral range of wavelengths corresponding to wavenumbers of from 200 cm$^{-1}$ to 5000 cm$^{-1}$ and more preferably from 650 cm$^{-1}$ to 4000 cm$^{-1}$. Although the entire spectral region scanned may be used in the PLS analysis, generally, the spectral region of conjunct polymer considered in the PLS analysis is preferably from 800 cm$^{-1}$ to 1800 cm$^{-1}$ (e.g., from 1300 cm$^{-1}$ to 1400 cm$^{-1}$) when modeling the conjunct polymer analytes.

Using the PLS analysis techniques therefore, chemometric models used to determine the concentration of conjunct polymer analytes as a function of the absorption spectrum may be developed and used in combination with the FTIR spectrometer to provide real-time concentration data for process mixtures from either a batch or a continuous process thus allowing for improved studies of the reaction kinetics, improved reaction control, and in the case of the batch processes, a more accurate and timely reaction end point determination to be made.

For example, using the techniques described above, chemometric models have been developed using an FTIR spectrometer and a diamond-composite ATR probe such that the concentration of conjunct polymer in spent ionic liquid may be measured over a range of concentrations of from about the detection limit, currently about 50 ppm, to about 7% with a PLS mean error of less than about 0.2% for a continuous alkylation process.

Figure 3:
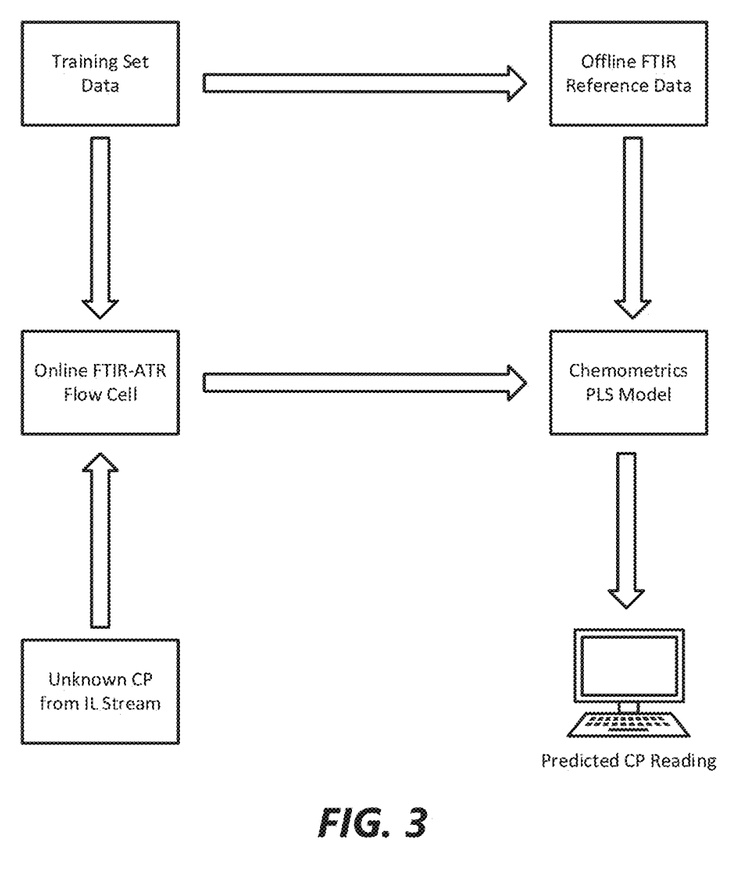
FIG. 3 is a flow chart illustrating example steps that can be performed to analyze infrared spectroscopic information of a spent ionic liquid, according to some aspects of this disclosure.

FIG. 3 is a flow chart illustrating example steps that can be performed to analyze infrared spectroscopic information of a spent ionic liquid, according to some aspects of this disclosure.

EXAMPLES

The following illustrative examples are intended to be non-limiting.

EXAMPLE

In a pilot plant alkylation unit using an acidic ionic liquid to make alkylate gasoline blending components, a Bruker FTIR spectrometer ALPHA II configured with an ATR cell was installed at a spent ionic liquid stream. Online FTIR spectral data were continuously collected at one-minute intervals using a flow cell with a DIGS detector. For each spectrum, 32 scans were collected at 4 cm$^{-1}$ resolution.

Figure 4:
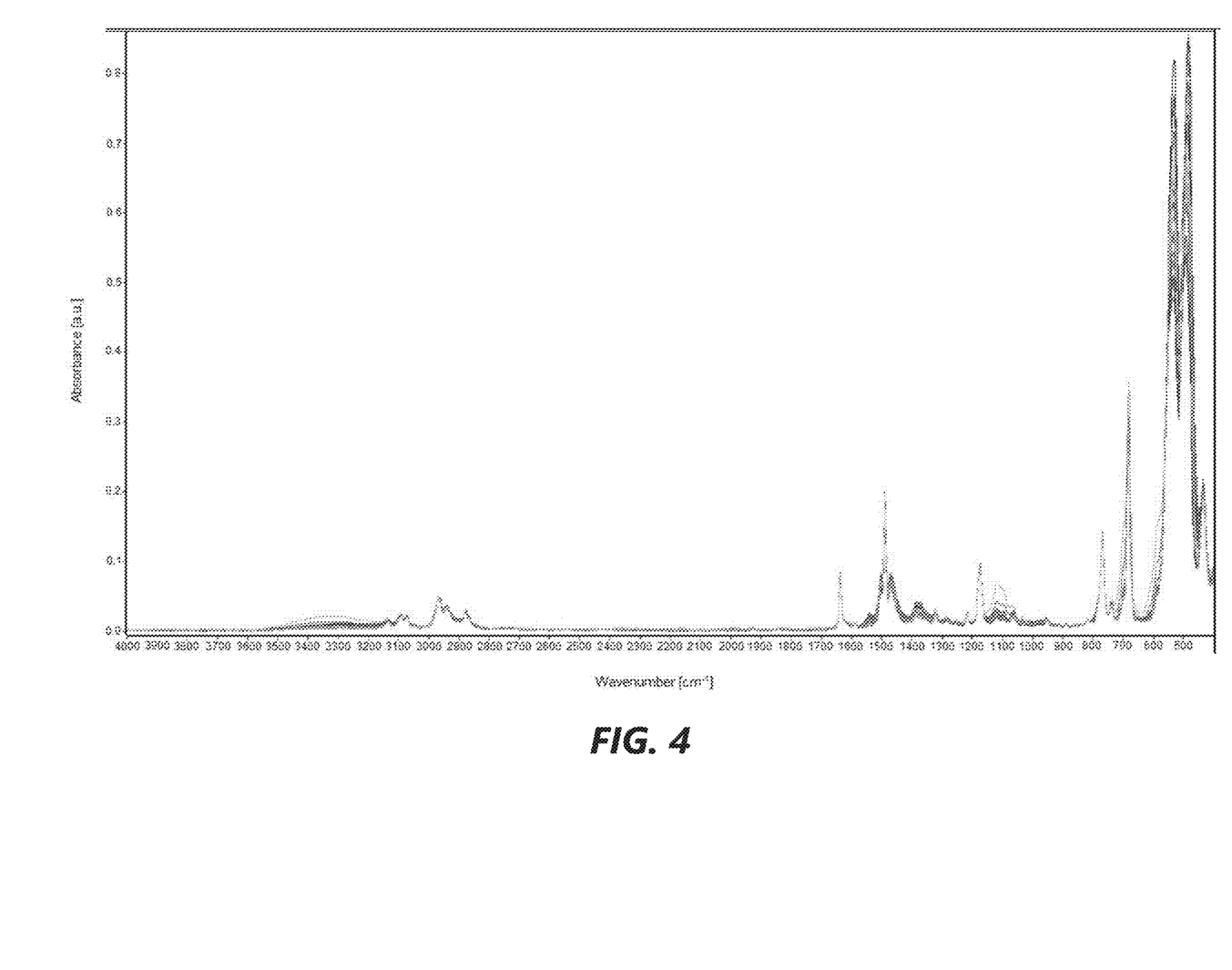
FIG. 4 is graph showing an overlay of Fourier-transform infrared (FTIR) absorbance spectra of conjunct polymer at various concentrations in spent ionic liquid.

Additionally, 360 spent ionic liquid samples were collected over a two-month period and were analyzed offline on a Bruker ALPHA II ATR-FTIR spectrometer using 8 scans at 4 cm$^{-1}$ resolution to obtain the concentration of conjunct polymer in spent ionic liquid (conjunct polymer concentration range of 0 to 6 wt. %). FIG. 4 is graph showing an overlay of FTIR absorbance spectra of conjunct polymer calibration samples.

FTIR spectral data were obtained within spectral regions from 800 to 1800 cm$^{-1}$ which includes the absorption bands associated with conjunct polymer components (at 1300 to 1400 cm$^{-1}$) by utilizing multivariate mathematical analysis of spectral data from the continuous alkylation process. Development of cross-validated PLS regression models for quantitation of conjunct polymer in spent ionic liquid was performed using Bruker QUANT2 chemometric software (v. 7.3). A set of 178 samples with a representative variation in conjunct polymer composition was created and used for the development of a cross-validated calibration and as a performance test. Another set of 169 samples was not included in the calibration and was validated across the calibration range.

Figure 5:
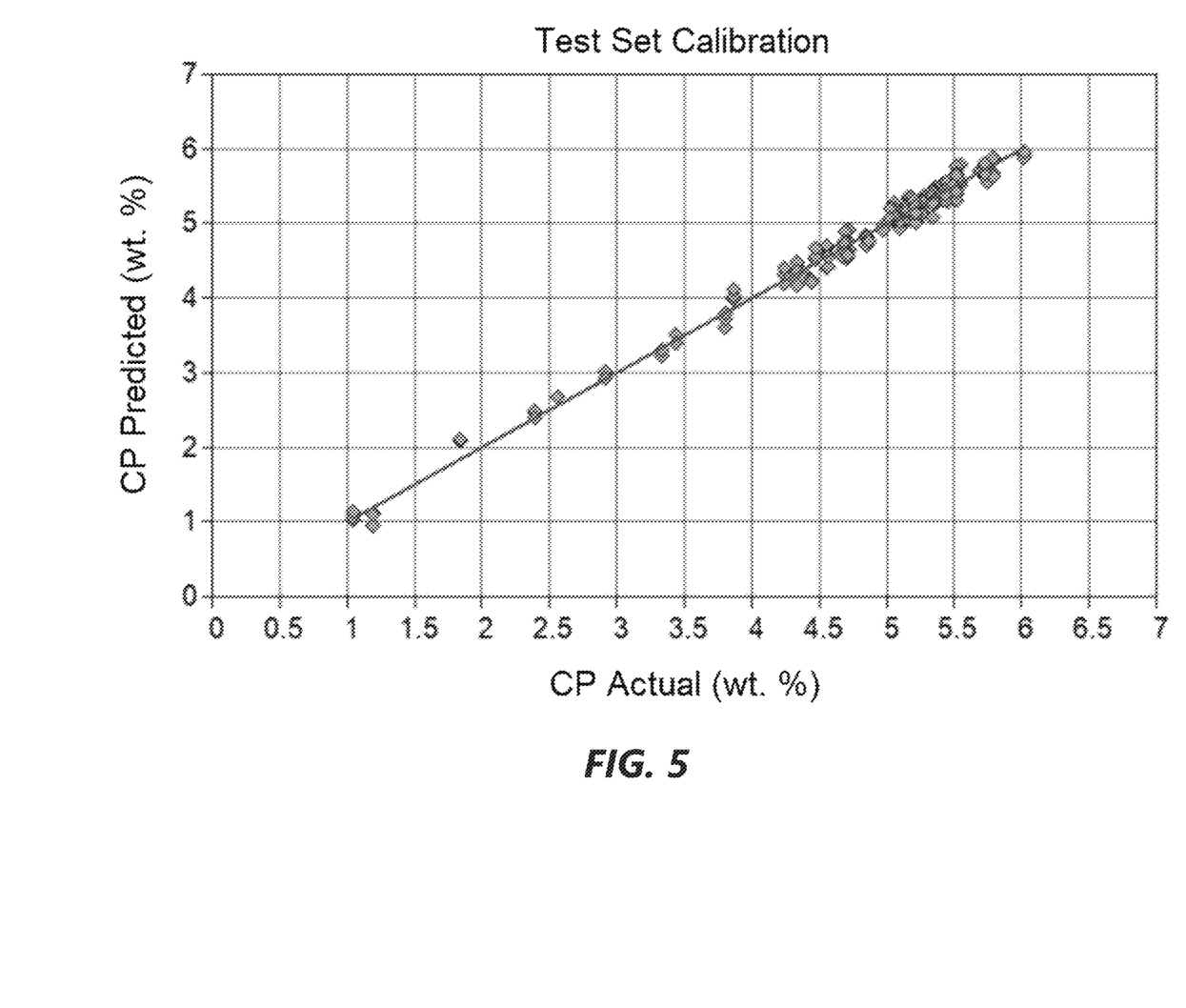
FIG. 5 is a graph illustrating calibration of predicted conjunct polymer (CP) concentration versus actual conjunct polymer of spent ionic liquid samples a using partial least squares (PLS) chemometric model.

FIG. 5 is a graph illustrating calibration of predicted conjunct polymer concentration versus actual conjunct polymer of spent ionic liquid samples a using PLS chemometric model. The resulting calibration model shown in FIG. 5 had a correlation coefficient ($R^2$) of 98.92 and a Root Mean Square Error of Estimation (RMSEE) of 0.111, which indicated promising findings.

Figure 6:
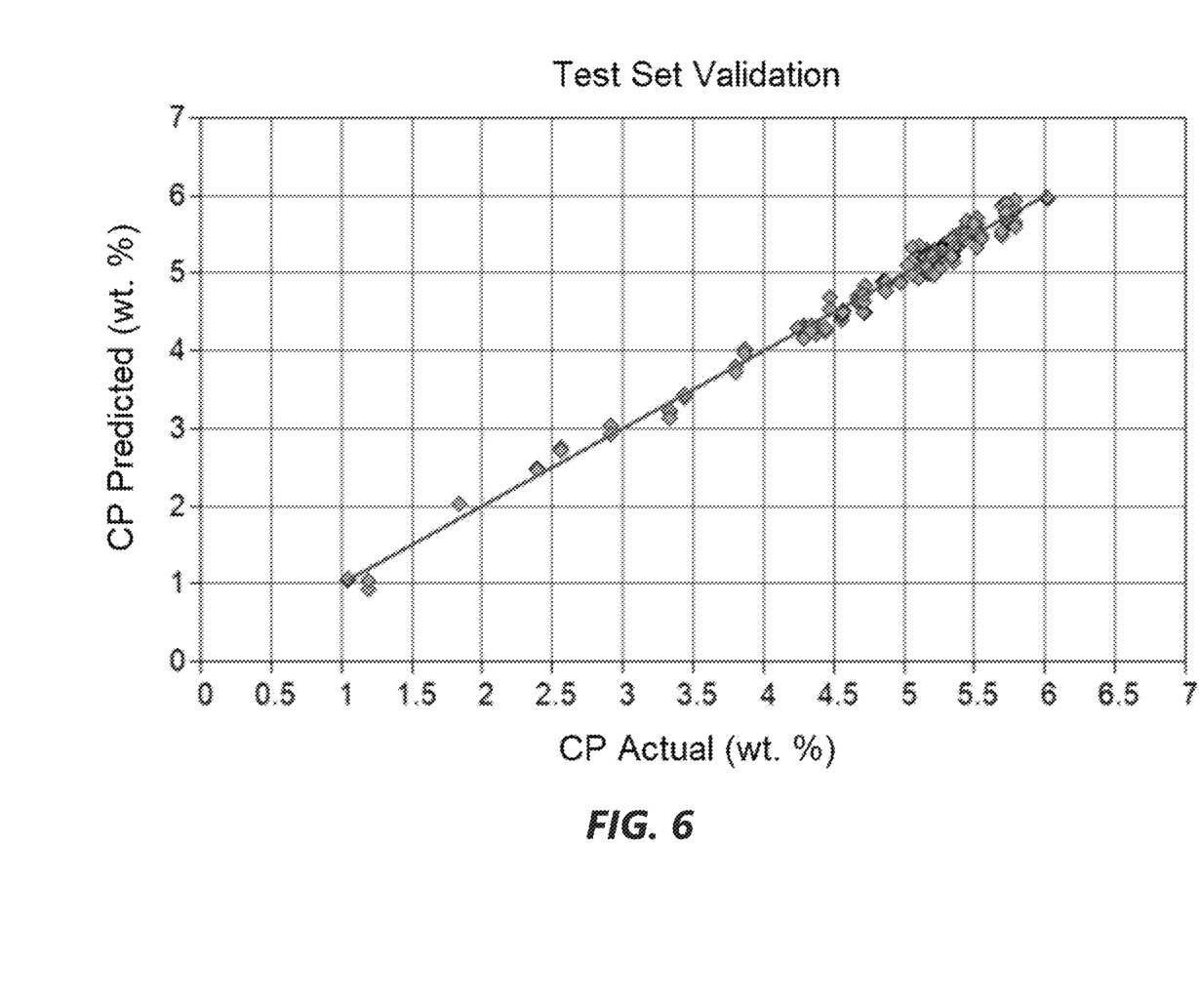
FIG. 6 is a graph illustrating a validation of calculated conjunct polymer (CP) concentration versus actual conjunct polymer concentration determined for off-line spent ionic liquid samples.

FIG. 6 is a graph illustrating a validation of calculated conjunct polymer concentration versus actual conjunct polymer concentration determined for spent ionic liquid samples. The resulting validation model shown in FIG. 5 had a correlation coefficient ($R^2$) of 98.81 and a Root Mean Square Error of Prediction (RMSEP) of 0.108. The validation model demonstrates that online measurement of conjunct polymer concentration in an alkylation stream is achievable with very high precision, thus allowing for in-situ monitoring of conjunct polymer concentration.

Figure 7:
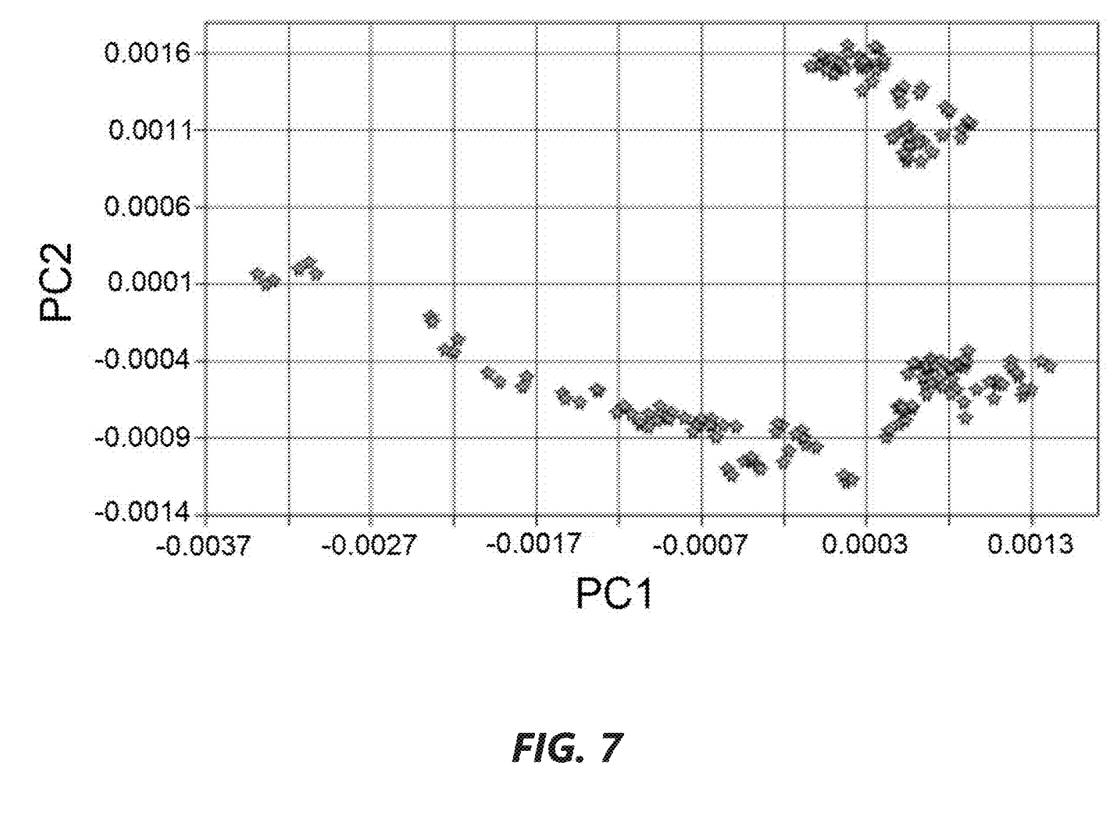
FIG. 7 is graph illustrating two-dimensional plots showing Principal Component Analysis (PCA) scores from a multivariate analysis of FTIR measurements in accordance with the present teachings.

In order to further explore the threshold values of concentration for a reliable test, a Principal Component Analysis (PCA) was applied to two series of a conjunct polymer data sets. In FIG. 7, the lower trace shows a first background data set while the upper trace shows a second background data set after cleaning the ATR window of the FTIR spectrometer and subsequently collecting a new background data set. PCA analysis with the first derivative IR of different analyses show that the two data sets did not affect the PLS model. However, once a final PLS model is built, PCA analysis is used to calculate from the IR absorption spectra and predict unknown online conjunct polymer samples.

Figure 8:
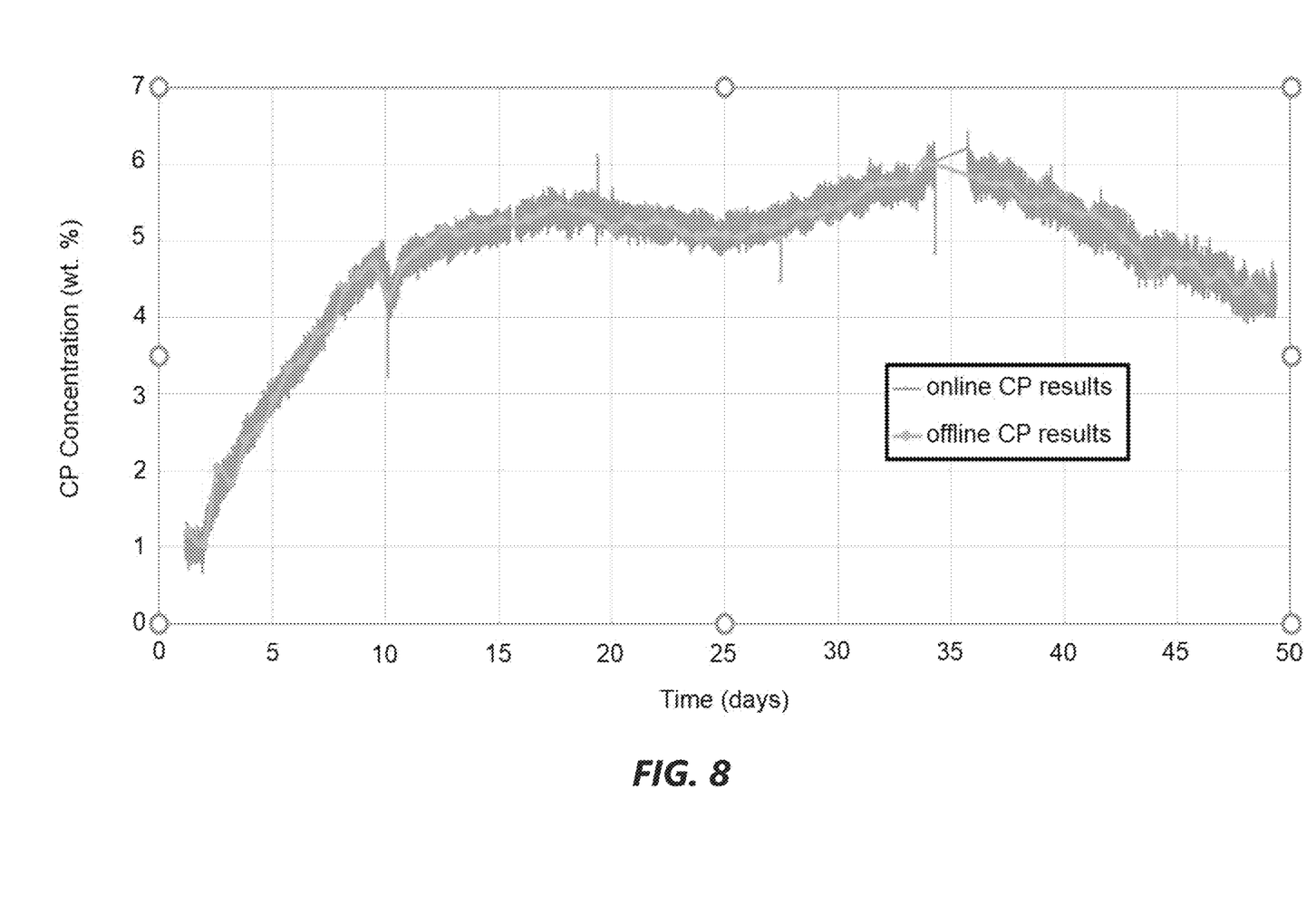
FIG. 8 is a graph illustrating conjunct polymer concentration, in-line prediction and off-line determination, in the spent ionic liquid stream during an alkylation over a two-month period.

FIG. 8 is a graph illustrating conjunct polymer concentration in the spent ionic liquid stream during alkylation over a two-month period. As shown, the trend in predicted online conjunct polymer concentration values versus offline conjunct polymer concentration values correlated very well. The presence of isobutane and buildup of fouling material on the ATR window of the FTIR spectrometer does not appear to be affecting this analysis even though the infrared backgrounds are different. The results show that a PLS model is capable of quantifying sample components when the correlation between concentration and absorbance even when the background changes, components may cause peaks in the mixture spectrum to shift or change, but the spectral variation present in the standards can accurately represent the variation expected in unknown conjunct polymer samples. The results further demonstrate that PLS multivariate calibration can provide high accuracy of conjunct polymer measurement and allows operators and engineers to respond much more quickly to even small changes in ionic liquid catalyst composition and/or activity.

The invention claimed is:

1. A method for predicting a concentration of conjunct polymer in a spent ionic liquid of unknown conjunct polymer concentration, during a continuous hydrocarbon conversion process, the method comprising:
   (a) contacting a hydrocarbon feed with an ionic liquid in a hydrocarbon conversion reaction zone under hydrocarbon conversion conditions to form a mixture comprising reaction products and spent ionic liquid containing conjunct polymer;
   (b) acquiring an infrared spectrum for each of a plurality of samples of the mixture in (a) using an in-line infrared spectrometer configured with a measurement flow cell to allow the mixture to flow therethrough, wherein absorbance values indicative of conjunct polymer are measured in each infrared spectrum over a wavenumber range of from 800 cm$^{-1}$ to 1800 cm$^{-1}$;

(c) collecting a sample from the mixture in (a) at each of a plurality of corresponding time points during the continuous hydrocarbon conversion process and separately determining off-line a concentration of conjunct polymer in the spent ionic liquid by acquiring a corresponding infrared spectrum for each sample using an off-line infrared spectrometer, wherein absorbance values indicative of conjunct polymer are measured in each infrared spectrum over a wavenumber range of from 800 $cm^{-1}$ to 1800 $cm^{-1}$;

(d) analyzing the infrared spectra acquired in (b) and (c) using a multivariate chemometric technique to provide a training data set, wherein the multivariate chemometric technique comprises a partial least squares (PLS) analysis;

(e) generating a predictive model for conjunct polymer concentration based on the training data set, wherein the predictive model is established using partial component analysis (PCA);

(f) applying the predictive model to the infrared spectra acquired in (b); and thereafter (g) quantitatively predicting the conjunct polymer concentration in the spent ionic liquid during the continuous hydrocarbon conversion process.

2. The method of claim 1, wherein the hydrocarbon conversion process comprises at least one of alkylation, disproportionation, isomerization, and oligomerization.

3. The method of claim 2, wherein the alkylation comprises contacting an isoparaffin feed having from 4 to 10 carbon atoms and an olefin feed having from 2 to 10 carbon atoms in the presence of the ionic liquid in an alkylation zone under alkylation conditions to generate an alkylate.

4. The method of claim 1, wherein acquiring the infrared spectrum in (b) and/or (c) comprises acquiring an attenuated total reflectance Fourier transform infrared spectrum.

5. The method of claim 1, further comprising:
controlling at least one of the following based upon the predicted conjunct polymer concentration in (g):
(i) an amount of spent ionic liquid passed back to the reaction zone;
(ii) an amount of spent ionic liquid passed to a regeneration zone;
(iii) an amount of regenerated ionic liquid passed back to the reaction zone;
(iv) an amount of fresh ionic liquid passed to the reaction zone; and
(v) an amount of spent ionic liquid catalyst removed from the continuous hydrocarbon conversion process.

6. The method of claim 1, further comprising:
maintaining a desired concentration range of conjunct polymer in the spent ionic liquid.

7. The method of claim 1, further comprising:
lowering a portion of spent ionic liquid returned to the reaction zone if a concentration of conjunct polymer in the spent ionic liquid is above a desired range.

8. The method of claim 7, further comprising:
passing a fresh ionic liquid, a regenerated ionic liquid, or both to the reaction zone if the concentration of conjunct polymer in the spent ionic liquid is above the desired range.

9. The method of claim 1, wherein the predicting of the concentration of conjunct polymer in the spent ionic liquid during the continuous hydrocarbon conversion process is performed in real-time or near real-time.

10. The method of claim 1, wherein in (c), at least 50 samples are collected.

11. The method of claim 1, wherein the spent ionic liquid containing conjunct polymer has a concentration of conjunct polymer that ranges from 50 ppm to 7% by weight conjunct polymer.

* * * * *